United States Patent [19]

Koths et al.

[11] Patent Number: 4,572,798
[45] Date of Patent: Feb. 25, 1986

[54] METHOD FOR PROMOTING DISULFIDE BOND FORMATION IN RECOMBINANT PROTEINS

[75] Inventors: Kirston E. Koths, Berkeley; Robert F. Halenbeck, San Rafael, both of Calif.

[73] Assignee: Cetus Corporation, Emeryville, Calif.

[21] Appl. No.: 679,121

[22] Filed: Dec. 6, 1984

[51] Int. Cl.$^4$ .................... C07G 7/00; A61K 45/02
[52] U.S. Cl. .................. 260/112 R; 260/112.5 R; 424/85; 435/811
[58] Field of Search ............... 260/112 R; 424/85; 435/811

[56] References Cited

U.S. PATENT DOCUMENTS

| | | | |
|---|---|---|---|
| 4,450,103 | 5/1984 | Konrad et al. | 260/112 R |
| 4,490,289 | 12/1984 | Stern | 260/112 R |
| 4,530,787 | 7/1985 | Shaked et al. | 260/112 R |

FOREIGN PATENT DOCUMENTS 114507  8/1984  European Pat. Off. .

OTHER PUBLICATIONS

*Bull. Chem. Soc. Japan,* 56, 2065–2068, (1983), Hanaki et al.
*Journal of Biochemistry,* 64, 449–455 (1968), Yutani et al.
*The Chemistry and Biochemistry of the Sulfhydryl Groups in Amino Acids, Peptides & Proteins,* N.Y.; Pergamon Press, Chapter 2, pp. 25–50 (1973).
*The Proteins* (1978), vol. III, 255–263 (Academic Press, N.Y.), Liu.
Leslie, J. et al., *Can. Jour. Biochem.,* 46, 625 (1968).
Kobashi, K., *Biochim. Biophys. Acta.,* 158, 239 (1968).
Price, P. et al., *J. Biol. Chem.,* 244, 929 (1969).

*Primary Examiner*—Howard E. Schain
*Attorney, Agent, or Firm*—Albert P. Halluin; Janet E. Hasak

[57] ABSTRACT

Reduced cysteine-containing proteins consisting of recombinant IFN-$\beta$, IL-2 or muteins thereof may be oxidized selectively so that the recombinant proteins have essentially the same disulfide bridging and biological activity as their native counterparts. The oxidized product is substantially free of unwanted side products and contains a minimal amount of intermolecular oligomers. The oxidation takes place in an aqueous medium containing a solubilizing agent at a pH of about 5.5 to 9, preferably at a pH of about 7. The reaction is initiated by addition of at least an effective amount of an oxidation promoter containing a $Cu^{+2}$ cation such as $CuCl_2$ or o-phenanthroline/$Cu^{+2}$ complex in the presence of air.

19 Claims, 20 Drawing Figures

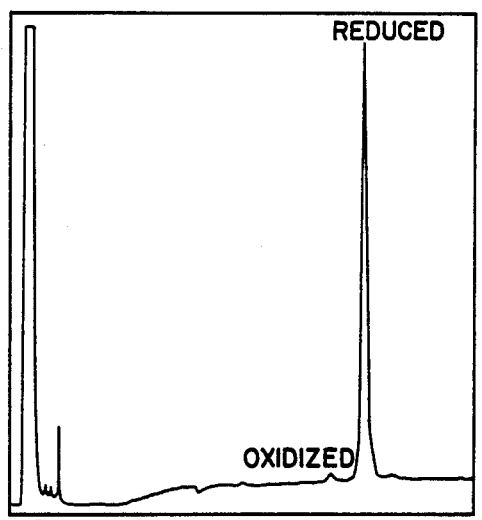
FIG._1A. CONTROL (NO Cu++, 7min)
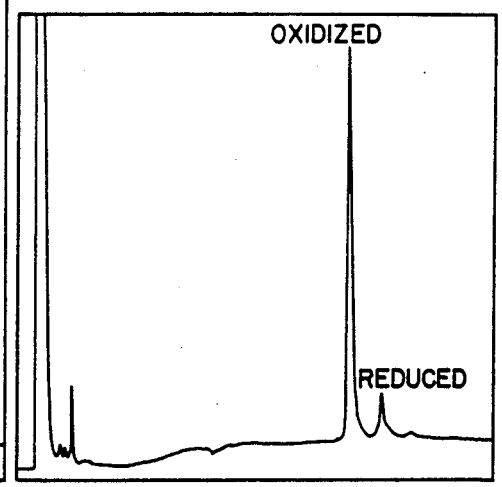
FIG._1D. (Cu++, 28min)
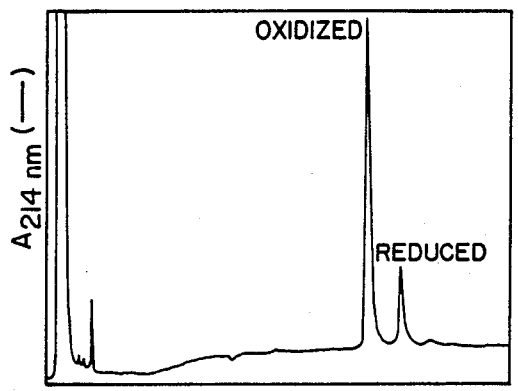
FIG._1B. (Cu++, 7min)
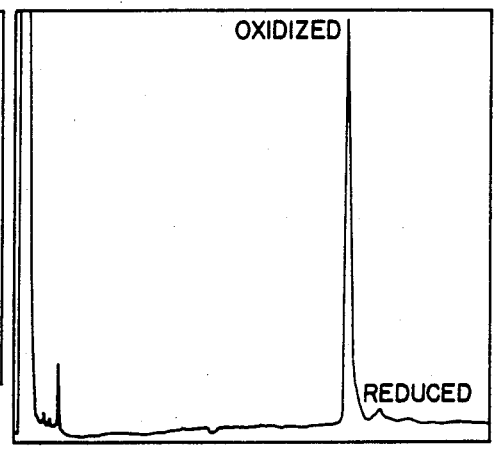
FIG._1E. (Cu++, 75min)
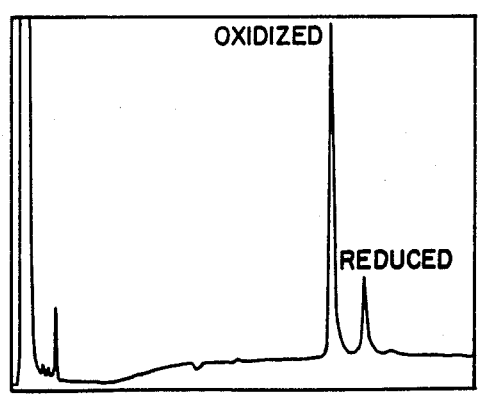
FIG._1C. (Cu++, 14min)
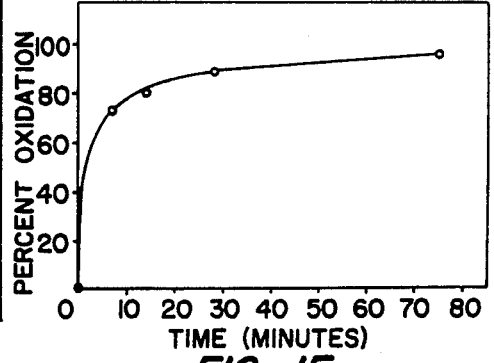
FIG._1F.

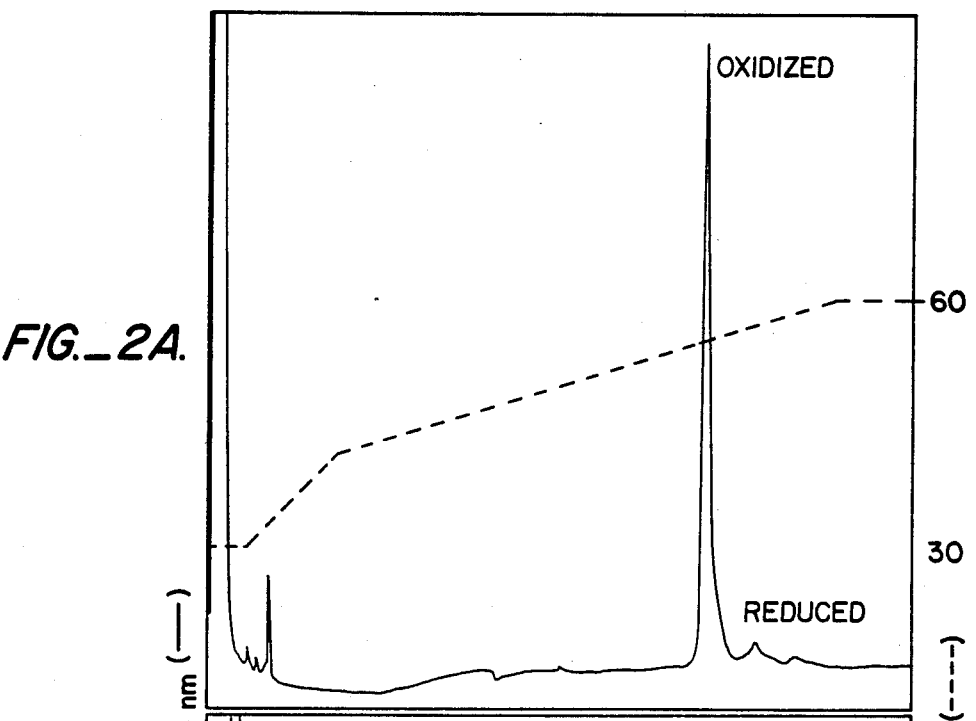
FIG._2A.
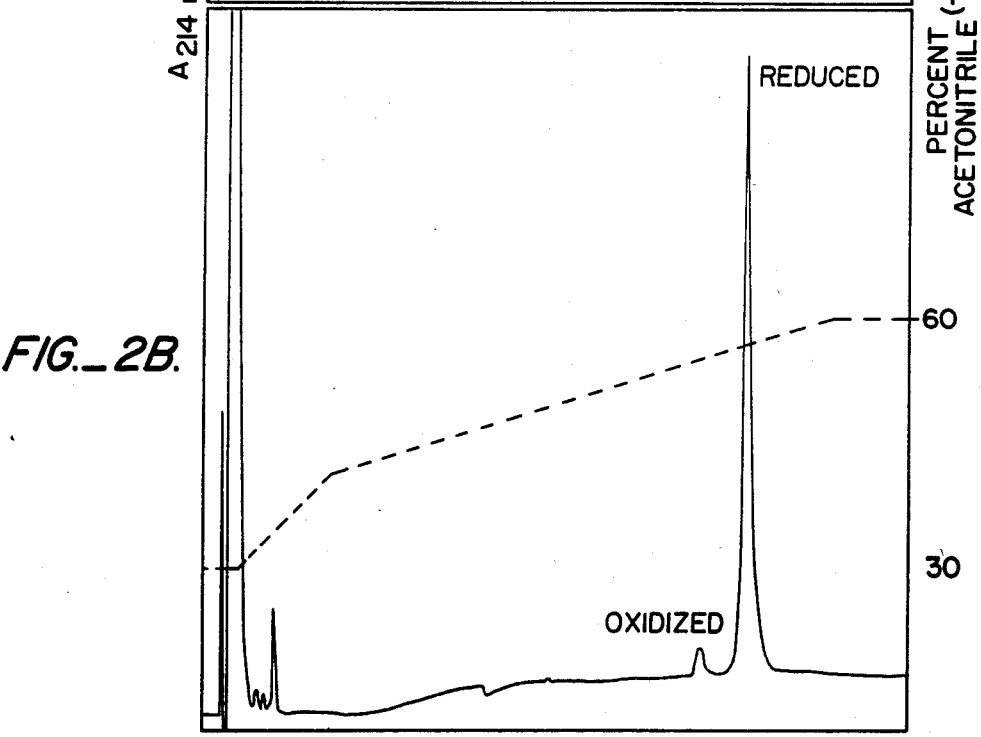
FIG._2B.

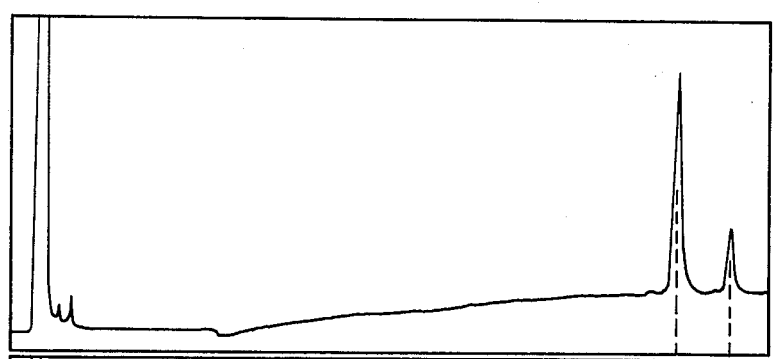
FIG._3A.
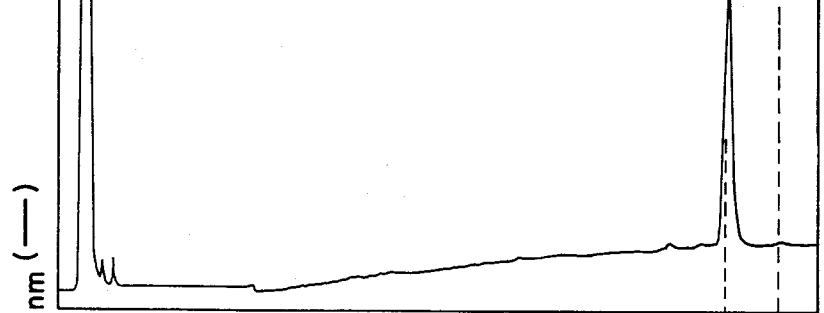
FIG._3B.
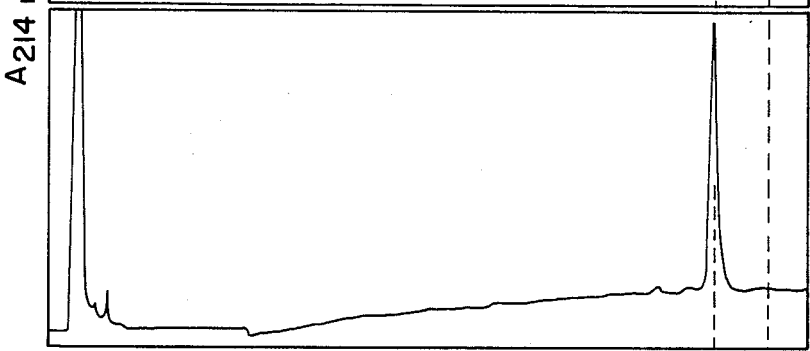
FIG._3C.
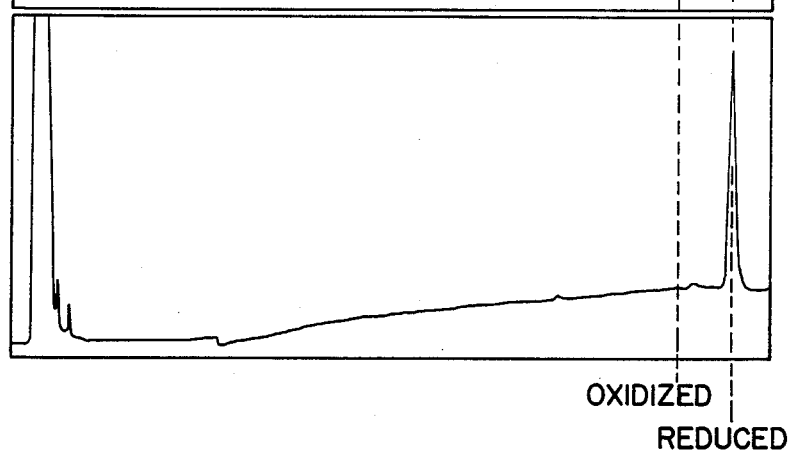
FIG._3D.
OXIDIZED
REDUCED (Silver Stained)

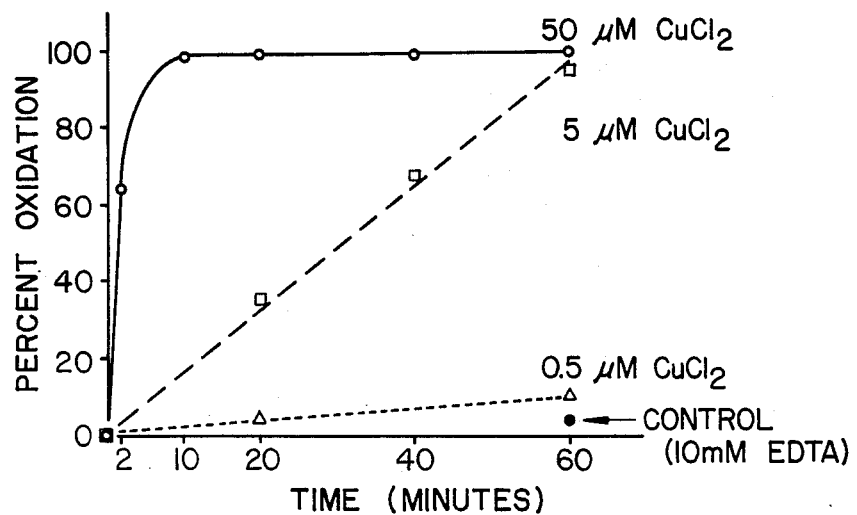
FIG._5.
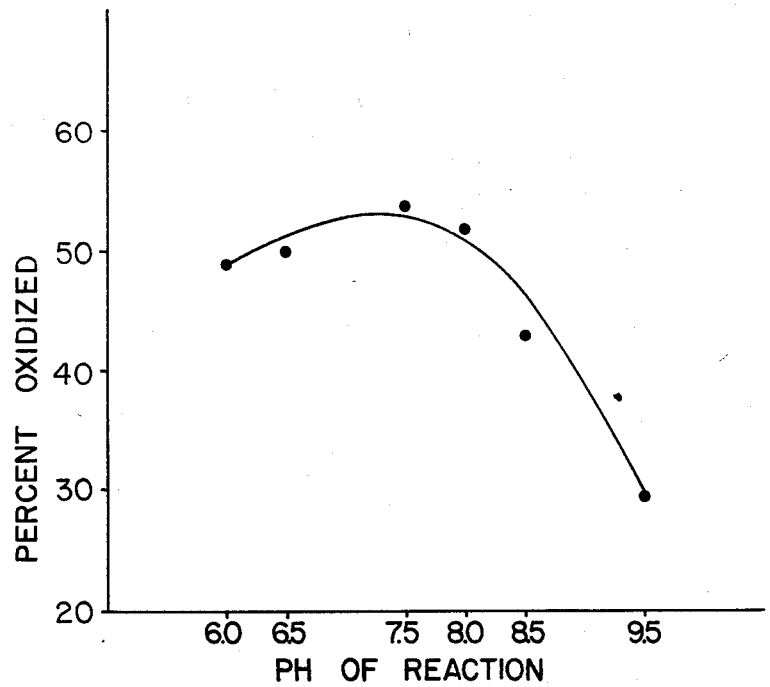
FIG._6.

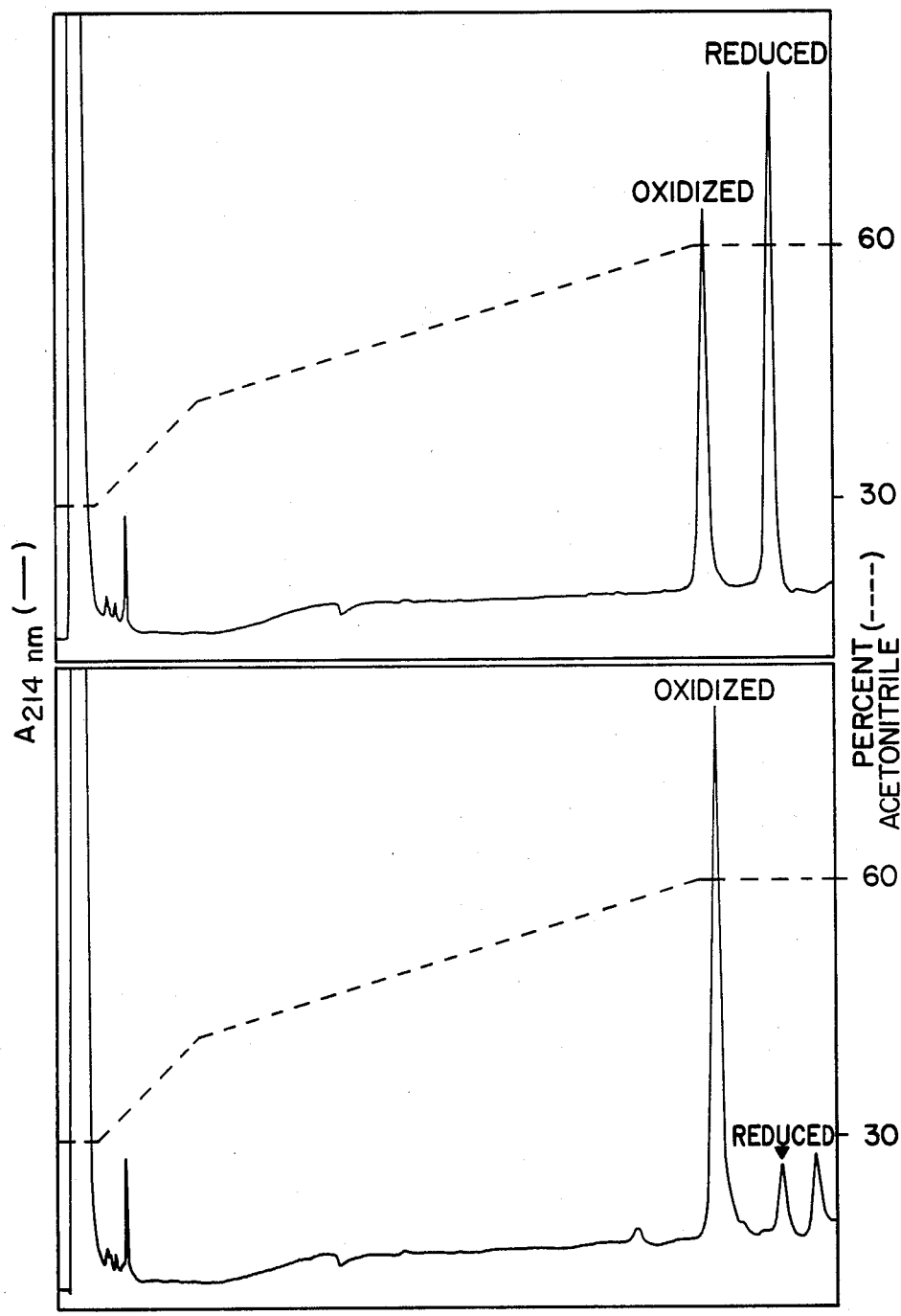

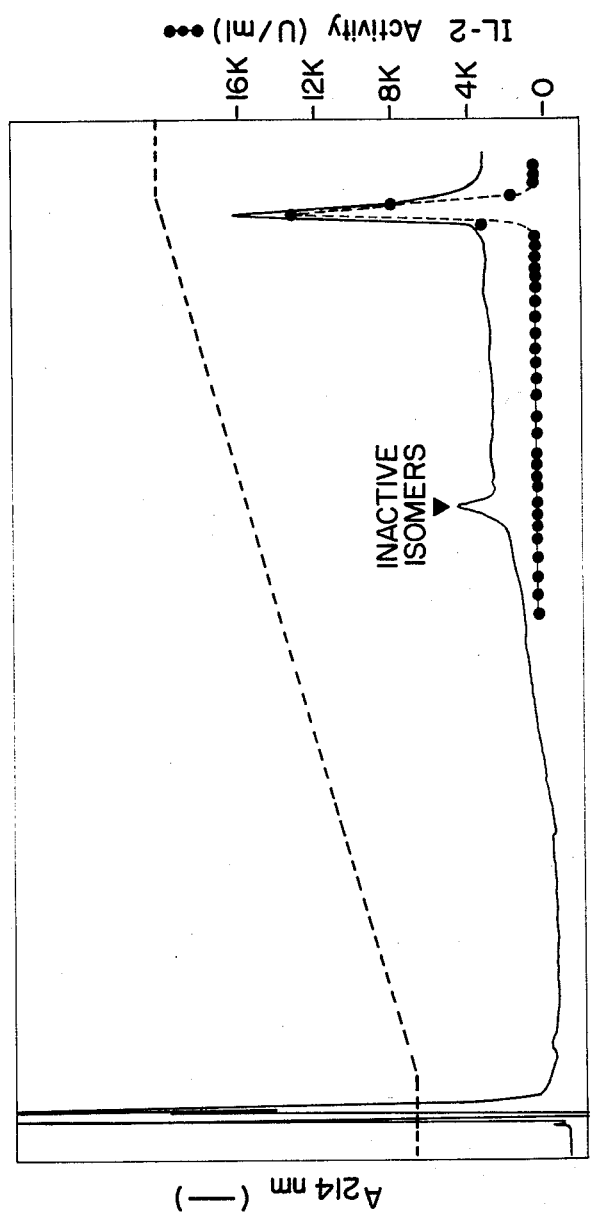
FIG._10.

METHOD FOR PROMOTING DISULFIDE BOND FORMATION IN RECOMBINANT PROTEINS

BACKGROUND OF THE INVENTION

1. Field of the Invention

This invention relates to a method of catalyzing disulfide bond formation in fully reduced, cloned gene products produced in microbes such as Escherichia coli. More particularly, the invention concerns such a method of oxidation wherein the reaction is controlled to promote the in vitro formation of disulfide bridges which correspond to those present in the naturally occurring protein species.

2. Description of Related Disclosures

When native proteins which contain one or more disulfide bridges in their native state are produced as recombinant proteins in microorganisms, the protein produced is often in a reduced form, lacking disulfide bridges. In some cases the protein product may contain oligomers following purification. Such oligomers may be the result of uncontrolled oxidation or thiol-disulfide exchange reactions. If the native protein contains disulfide bonds, it will often be desirable to promote chemically the formation of the corresponding disulfide bonds in the recombinant protein product, while minimizing the formation of oligomers or other modified protein by-products. Oxidizing the protein in an uncontrolled manner may also result in the formation of undesirable isomers (incorrect intramolecular bridging). Such unwanted reactions may complicate the purification of the protein from the culture, reduce the yield of protein having the desired structure, or generate a protein with less than full bioactivity. In the case of certain proteins which are intended for therapeutic use, uncontrolled disulfide bond formation during purification or formulation may yield a nonhomogeneous material which is contaminated with isomers and/or oligomers which may be inactive and/or have increased immunogenicity.

U.S. Pat. No. 4,530,787 issued July 23, 1985 to Ze'ev Shaked et al., entitled "Controlled Oxidation of Microbially Produced Cysteine-Containing Proteins," describes a process for oxidizing such microbially produced proteins in a selective, contolled manner using a non-catalytic oxidizing agent, preferably o-iodosobenzoic acid, which oxidizes cysteines preferentially producing the desired disulfide bridging in high yield. This process requires at least stoichiometric amounts of oxidizing agent to protein to ensure that the oxidation proceeds to completion.

Similarly, a process has been described for the catalysis of disulfide bond formation in microbially produced rennet, using a mixture of oxidized and reduced glutathione in urea. (European patent application No. 83307841.3 published as European Publication No. 114,507 on Aug. 1, 1984 to Hayenga et al.)

It is known that ferricyanide or copper +2 ions are able to catalyze disulfide bond formation in β-lactoglobulin in the presence of sodium dodecyl sulfate. Leslie, J. et al., Can. Jour. Biochem., 46, 625 (1968). Other disclosures teach use of specific divalent metal salts as oxidants for cysteine or the sulfhydryl groups in specific cases: (a) copper ion: (for free crysteine) Hanaki, A. et al., Bull Chem. Soc. Jpn., 56, 2065 (1983); (for sulfhydryls in lysozyme) Yutani, K. et al., J. Biochem., 64, 449 (1968); (for sulfhydryl compounds such as glutathione, cysteine, 2-mercaptoethanol, thiogly- colic acid and reduced lipoic acid) Kobashi, K., Biochim. Biophys. Acta, 158, 239 (1968); (b) transition metals: (for cysteine and other mercaptans and proteins with free sulfhydryl groups) Friedman, Mendel, The Chemistry and Biochemistry of the Sulfhydryl Group in Amino Acids, Peptides and Proteins, (New York: Pergamon Press), Chapter 2, pp. 25-50 (1973); and (c) possibly calcium ion: (for sulfhydryls in deoxyribonuclease) Price, P. et al., J. Biol. Chem., 244, 929 (1969).

The mechanism of oxidation in these reactions is unclear, but has been postulated to be based on reactions involving peroxide or free radicals. However, it appears that the ability to predict that a given divalent salt will successfully promote the correct oxidation of a specific protein without extensive side reactions is not possible at this time. The present invention demonstrates the ability of certain metal-containing compounds to promote highly selective and useful formation of disulfides in various forms of recombinant interleukin-2 and β-interferon.

SUMMARY OF THE INVENTION

The present invention relates to a method of oxidizing a fully reduced recombinant protein selected from the group consisting of interferon-beta, interleukin-2 and muteins thereof, whereby cysteines are oxidized preferentially to form the disulfide bridges which correspond to those present in the naturally occurring protein. This method comprises reacting an aqueous solution containing a solubilized form of the recombinant protein at a pH of between about 5.5 and 9 in the presence of air with at least an effective amount of an oxidation promoter containing a $Cu^{+2}$ cation.

The method of this invention minimizes the difficulties encountered during oxidation of specific proteins, including oxidative side reactions, inability to regain full bioactivity, and unwanted oligomer or isomer formation. In addition, the preferred method herein described, using cuprous chloride as an oxidation promoter, has the added advantages of being extremely rapid and involving a reagent which is easily assayable in and easily removed from the final product. The reaction herein described is active at catalytic as well as stoichiometric concentrations (relative to free sulfhydryls). Thus, the need to monitor the mole ratio of oxidation promoter to protein (in order to achieve 100% disulfide formation) may not be as great as with other oxidation agents. Disulfide bond formation in recombinant interleukin-2 (rIL-2) or β-interferon (rIFN-β) at mg/ml concentrations can be driven to completion in one hour at $CuCl_2$ concentrations of less than 100 μM.

BRIEF DESCRIPTION OF THE DRAWINGS

FIG. 1 represents five reverse-phase high pressure liquid chromatography (RP-HPLC) absorbance profiles of a reaction mixture in which a recombinant mutein of IFN-β, having its cysteine residue at position 17 replaced by a serine residue (designated herein as IFN-$\beta_{ser17}$), has been oxidized using 8 μM $CuCl_2$ as the oxidation promoter. FIG. 1A represents a control reaction involving reduced IFN-$\beta_{ser17}$ which has been placed in a buffer for 7 minutes without $CuCl_2$. FIG. 1B represents 7 minutes of oxidation with $CuCl_2$; FIG. 1C represents 14 minutes of oxidation; FIG. 1D represents 28 minutes of oxidation; and FIG. 1E represents 75 minutes of oxidation. FIG. 1F represents a plot of the percent IFN-$\beta_{ser17}$ oxidized versus number of minutes of oxidation, based on the RP-HPLC analysis.

FIG. 2 provides a comparison of recombinant IFN-$\beta_{ser17}$ after oxidation for 75 minutes in 8 µM CuCl$_2$ (FIG. 2A) with an aliquot of the same material reduced for 15 minutes in 10 mM dithiothreitol at 50° C. (FIG. 2B).

FIG. 3 represents four RP-HPLC absorbance profiles of a reaction mixture in which a recombinant mutein of IL-2, having the cysteine residue at position 125 replaced by a serine residue and having the N-terminal alanine deleted (designated herein as des-ala IL-2$_{ser125}$), has been oxidized using 50 µM CuCl$_2$ as the oxidation promoter. FIG. 3A represents 2 minutes of oxidation; FIG. 3B represents 10 minutes of oxidation; FIG. 3C represents 50 minutes of oxidation; and FIG. 3D represents a chromatogram of the reaction mixture after the oxidized product of 50 minutes is re-reduced using 10 mM dithiothreitol for 15 minutes at 60° C.

FIG. 5 represents plots of the percent oxidation of the des-ala IL-2$_{ser125}$ (as measured by HPLC peak height, less background) versus time in minutes at 25° C. for three different CuCl$_2$ concentrations. A control reaction containing 10 mM ethylenediamine tetraacetic acid (EDTA) was also run.

FIG. 6 represents a plot of the percent oxidation of the des-ala IL-2$_{ser125}$ (as measured by HPLC peak height, less background) versus the pH of the oxidation reaction using 8 µM CuCl$_2$. The plot shows the effect of varying pH on the reaction rate measured at the point in the reaction at which IL-2 is approximately 50% oxidized.

FIG. 7 represents the oxidation of des-ala IL-2$_{ser125}$ using o-phenanthroline/Cu$^{+2}$ complex (FIG. 7B) compared with oxidation using CuCl$_2$ (FIG. 7A).

FIG. 10 represents a RP-HPLC absorbance profile of the product of oxidation of des-alanyl IL-2 (containing the three cysteines present in native IL-2) promoted by 50 µM CuCl$_2$.

DESCRIPTION OF THE PREFERRED EMBODIMENTS

Figure 4:
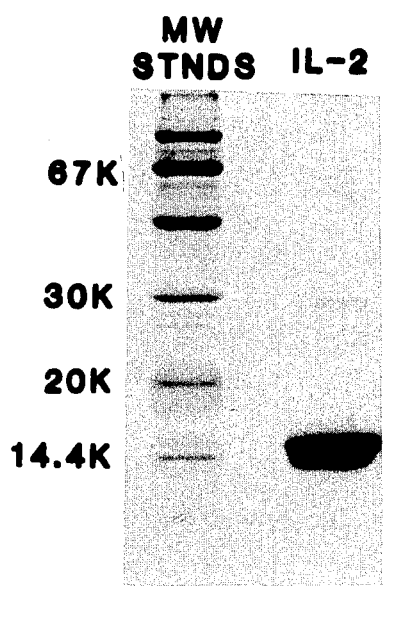
FIG. 4 represents a silver-stained, non-reducing SDS-PAGE analysis of the des-ala IL-2$_{ser125}$ protein after 40 minutes of oxidation using 50 µM CuCl$_2$ as the oxidation promoter to determine the extent of formation of intermolecular sulfhydryl groups (oligomers).

The recombinant proteins which are oxidized by the method of this invention are not native to the hosts used to produce them. Both IL-2 and β-IFN have amino acid sequences which are substantially identical to useful proteins and include cysteine residues which in the useful protein are linked intramolecularly to form a single cystine moiety (disulfide bridge). In this regard the term "substantially identical" means that the amino acid sequences of the recombinant and useful proteins are either identical or differ by one or more amino acid alterations (e.g., deletions, additions, or substitutions) which do not cause an adverse functional dissimilarity between the recombinant protein and its native counterpart. The recombinant proteins which are oxidized in the process of this invention are fully reduced, i.e., they lack disulfide bridging. For a protein such as interleukin-2 to be a uniform substrate for oxidation, it is usually reduced prior to the oxidation process. Reduction may be accomplished by treating the protein with a reducing agent such as dithiothreitol or 2-mercaptoethanol at an elevated temperature for a short period of time. The reducing agent is then removed immediately prior to the oxidation reaction.

The recombinant proteins to be oxidized by the process of this invention may be generated using established genetic engineering techniques. These techniques involve identifying and characterizing the structural gene which encodes the native protein, isolating or synthesizing that gene or a mutant which encodes a functionally equivalent mutein of the native protein, inserting the gene into an appropriate expression vector in a position which permits expression of the gene, transforming competent heterologous hosts, preferably microorganisms, with the vector, identifying correct transformants, and culturing the transformants in a suitable growth medium. The protein is typically recovered from the culture by disrupting the cells, treating the cellular debris with solubilizing agents (depending on the solubility characteristics of the protein) and one or more extractants to isolate crude protein, and purifying the crude protein by various preparative chromatography procedures. If the protein is susceptible to oligomer formation during the fermentation or recovery processes, the protein will be treated with a reducing agent at an appropriate stage in the recovery process.

After the recombinant protein is recovered from the host in a crude, substantially pure, or pure form, it is reduced and then oxidized with controlled kinetics using the invention process. Controlled oxidation pursuant to the process of this invention causes the formation of disulfide bridging in the recombinant protein which conforms to the bridging in its native counterpart with no or minimal overoxidation and no or minimal formation of incorrect disulfides or unwanted oligomers. Such oxidation enables the production of high yields of the recombinant protein in a configuration which most closely resembles the configuration of its native counterpart, thereby ensuring the likelihood that the recombinant protein will be functionally equivalent to the native protein.

The term "recombinant protein" as used herein also refers to muteins of IL-2 and β-IFN. Such muteins include, for example, proteins in which one or more cysteines not involved in disulfide bridging have been replaced with another amino acid to eliminate sites for intermolecular crosslinking or incorrect intramolecular disulfide bond formation. Other IL-2 muteins in which amino acids besides cysteine have been replaced have also been constructed and are fully active.

A gene containing an undesirable and inessential cysteine can be selectively modified using a synthetic oligonucleotide primer complementary to the region of the gene but containing single or multiple base changes in the cysteine codon, resulting in a mutant protein (mutein) which now contains a different amino acid at that position. When deletion is desired the oligonucleotide primer would lack the codon for cysteine. Conversion of cysteine to neutral amino acids such as glycine, valine, alanine, leucine, isoleucine, tyrosine, phenylalanine, histidine, tryptophan, serine, threonine and methionine is the preferred approach. Serine, threonine, or alanine are preferred replacements because of their chemical similarity to cysteine. When the cysteine is deleted, the mature mutein is one amino acid shorter than the native parent protein.

Human IL-2 and IFN-$\beta$ both contain three cysteine residues in the mature protein. The presence of three cysteines means that upon reoxidation, these proteins may form one of three possible intramolecular disulfide bridges, only one of which corresponds to the correct bridge found in the native molecule. Muteins of IFN-$\beta$ and IL-2 in which inessential cysteines have been changed to serines are discussed in detail in Mark et al., (1984), *PNAS* (USA), 81, 5662–5666 and Wang et al., (1984), *Science,* 224, 1431–1433, respectively.

The oxidation promoter which is used in the process is an agent which is responsible for promoting the oxidation of cysteine residues preferentially and which contains a divalent copper cation. Other divalent cations such as $Fe^{+2}$ are much less effective as oxidation promoters. The $Cu^{+2}$ cation is found to produce pure oxidized protein with minimal by-products. The term "preferentially" indicates that the oxidation promoter (1) preferentially oxidizes the cysteines to form a disulfide bond with no or insignificant oxidation to higher levels, (2) preferentially oxidizes cysteines to form disulfide bridges which correspond to those present in the naturally occurring protein species, and (3) preferentially oxidizes cysteine residues as opposed to other residues. The oxidation promoter herein is capable of promoting oxidation of a mutein of IL-2 containing two cysteine residues so as to obtain at least 95% yield of the desired product with the cysteines oxidized to form disulfide bridges which correspond to those present in the naturally occurring protein. It is also capable of promoting oxidation of a mutein of IL-2 containing three cysteine residues so as to obtain at least 80–85% yield of the desired product. Examples of suitable oxidation promoters herein include $CuCl_2$ and (o-phenanthroline)$_2Cu^{+2}$ complex. Preferably, the oxidation promoter is $CuCl_2$.

The amount of oxidation promoter employed is at least an effective amount for oxidation, i.e., an amount which at minimum will be necessary to conduct the oxidation reaction effectively within a convenient period of time. This amount, and the optimum amount for each reaction, may depend specifically on such factors as, for example, the type of protein, the type of oxidation promoter, the reaction temperature, the pH of the reaction, and the type and concentration of the solubilizing agent. Altering the concentration of oxidation promoter and time for oxidation is also expected to affect the types and amounts of side products generated. For pharmaceutical purposes it will usually be necessary to remove substantially all of the side products as well as unoxidized starting material which could theoretically generate unwanted oligomers through thiol-disulfide exchange reactions. In the examples below an effective amount is the amount approximately equivalent to the concentration of free sulfhydryl groups on the protein which are destined to be involved in forming the desired disulfide bonds. This amount, of course, must be optimized for each protein according to criteria which include, but are not limited to, convenient reaction time, types and amounts of side products, pH, etc. It is likely that the independent variables interact in such a way that there may be no unique optimum set of conditions for all proteins.

FIG. 5, which illustrates the effect of $CuCl_2$ concentration on the rate of IL-2 oxidation, shows that the observed oxidation rate increases as the concentration of $CuCl_2$ increases from 0.5 to 50 $\mu$M. The reaction rate has also been shown to increase two-fold when the reaction is carried out at 37° C. rather than at room temperature (see Example 3). Thus, the reaction can be controlled to minimize potential for over-oxidation by simply adjusting the oxidation promoter concentration, the reaction time, or the reaction temperature. Preferably, the amount of $CuCl_2$ will range from about 1 to 400 micromolar, depending on the protein concentration, more preferably 5 to 50 micromolar if the protein is IL-2.

The concentration of protein in the reaction mixture is generally kept relatively low to reduce the likelihood of oligomer formation. Depending on the sulfhydryl content and the molecular weight of the protein which is being oxidized, the protein concentration is generally less than about 5 mg/ml, preferably about 0.05 to about 2 mg/ml, and more preferably about 0.1 to about 1 mg/ml.

The pH of the reaction medium is generally maintained at a level of between about 5.5 and 9. Use of pHs significantly above the pH range specified herein causes a significant decrease in the rate of oxidation using $CuCl_2$ as the oxidation promoter. The pH is preferably maintained between about 6 and 8, and more preferably about 7, as indicated by FIG. 6, which illustrates the effect of pH on the rate of IL-2 oxidation.

The reduced, cloned protein, which is less soluble than the oxidized form of the protein, generally must remain in solution, i.e., be in solubilized form, for effective oxidation to occur. Therefore, the reaction mixture will preferably also contain at least an effective amount of a solubilizing agent to prevent the protein from precipitating out of the solution. As used herein, the term "solubilizing agent" refers to an ionic or nonionic protein-solubilizing solute such as, e.g., sodium dodecyl sulfate (SDS) or urea. The amount of solubilizng agent which may be employed for this purpose is generally from about 0.1 to about 1% by weight per volume (for detergents) or about 5–9M (for urea), depending mainly on the protein and types of oxidation promoter used.

The oxidation reaction time will depend, for example, upon the concentration of reagents in the reaction mixture, the reaction temperature and the types of reagents. The reaction temperature will normally be between about 20° C. and about 40° C., conveniently room temperature, to maintain the solubilizing agent/protein mixture in solution. Increasing the reaction temperature increases the rate of reaction. For achievement of complete oxidation, the reaction time or temperature may be altered as appropriate for the particular process. The oxidation reaction may be effectively terminated by, for example, freezing the solution, adding chelators such as EDTA to the reaction mixture, or lowering the pH to a level at which the reaction ceases. Other factors such as concentration of solubilizing agent may also affect the rate of reaction. Following the reaction, residual oxidation promoter and undesired isomers or oligomers may be removed by selective ultrafiltration or chromatographic techniques. If necessary the oxidized protein may be purified further from side products and any residual reduced protein using protein purification procedures such as reverse phase high performance liquid chromatography (RP-HPLC). The extent of oxidation during the reaction is also readily quantifiable by RP-HPLC analysis.

Recombinant des-ala IL-$2_{cys125}$ contains three cysteines and is theoretically susceptible to incorrect disulfide bond formation. When this protein is oxidized by the method described herein, the resulting product consists of protein having mostly the disulfide bridging of its native counterpart (between cysteines at residues 58 and 105 [Wang, et al. (1984) *Science,* 224:1431–1433; Robb, et al. (1984) *PNAS,* 81:6486–6490]). The oxidized protein is substantially free of oligomers (less than about 1–2% by weight) and contains less than about 15% by weight of biologically inactive isomers which have disulfide bridging different from that of the native counterpart. In contrast, preparations made via uncontrolled oxidations may contain significant amounts of oligomers (5%–10%) and even larger amounts of undesired isomers. Uncatalyzed air oxidations proceed slowly over a matter of days and are very slow to reach completion.

Proteins which have been designed to eliminate the possibility of isomer formation (e.g., IL-2 in which the cysteine at position 125 has been changed to serine, or IFN-$\beta$ in which the cysteine at position 17 has been changed to serine), of course, contain no isomers. In the case of at least IL-2, the oxidized protein is much more water soluble than the reduced species and also has a higher specific activity in biological assays. Accordingly, the amount of the solubilizing agent (e.g., SDS) in the preparation may be decreased, generating a purified product which is sufficiently water soluble to permit formulation with conventional aqueous parenteral vehicles in a fashion suitable for use in humans or animals. In addition, this oxidized recombinant IL-2 mutein contains only the disulfide bridging present in IL-2 isolated from natural sources. The same procedure used above for the formation of disulfide bonds may be applied to other muteins of IL-2 to generate homogeneous, biologically active material.

Because the protein preparations prepared by the controlled oxidation typically contain more desired product and fewer by-products than preparations made via uncontrolled oxidation, they are expected to be less antigenic and possibly more therapeutically active.

Preparations of therapeutic proteins will comprise a therapeutically effective amount of the protein together with a pharmaceutically acceptable carrier. The preparation will generally be formulated for parenteral administration in vehicles such as distilled water, human serum albumin, and/or dextrose in water, or physiological saline.

The following examples further illustrate the invention process. These examples are not intended to limit the invention in any manner. In the examples all temperatures are in degrees Celsius.

EXAMPLE 1

Controlled Oxidation of Recombinant IFN-$\beta_{ser17}$

Preparation of IFN-$\beta_{ser17}$

IFN-$\beta_{ser17}$ is a microbially produced mutein of IFN-$\beta$ in which the cysteine residue at amino acid position 17 is replaced with a serine residue. IFN-$\beta_{ser17}$ has two remaining cysteine residues: one at position 31 and the other at position 141. In native IFN-$\beta$ the cysteines at positions 31 and 141 interact to form a disulfide bridge. The genetically engineered *E. coli* strain used in this example to produce IFN-$\beta_{ser17}$ was deposited in the American Type Culture Collection, 12301 Parklawn Drive, Rockville, Md. 20852 USA on Nov. 18, 1983 under accession No. 39,517.

The genetically engineered *E. coli* mentioned above was grown in the following medium:

| Ingredient | Approximate Initial Concentration |
| --- | --- |
| Na$_3$ Citrate.2H$_2$O | 3 mM |
| H$_2$PO$_4$ | 30 mM |
| (NH$_4$)$_2$SO$_4$ | 74 mM |
| MgSO$_4$.7H$_2$O | 3 mM |
| MnSO$_4$.H$_2$O | 46 $\mu$M |
| ZnSO$_4$.7H$_2$O | 46 $\mu$M |
| CuSO$_4$.5H$_2$O | 1–2 $\mu$M |
| L-tryptophan | 350 $\mu$M |
| FeSO$_4$.7H$_2$O | 74 $\mu$M |
| thiamine.HCl | 0.002% (w/v) |
| glucose | 0.5% (w/v) |

A 25% solution of Dow Corning Antifoam B, a 50% solution of glucose and 5N KOH were added on demand.

The temperature was maintained at 37±1° C., the pH at 6.5±0.1 with NaOH, and dissolved oxygen at 30% w/w of air saturation. Optical density and residual glucose measurements were taken at 14 hours and at approximately one-hour intervals thereafter. Harvest was e consumption reached 40±6 g/l (OD at 680 nm=10–11).

The harvested material was concentrated approximately 3-fold by circulating it through a microporous cross-flow filter under pressure. The concentrated cells were diafiltered against deionized water until the harvest material was concentrated 4–5 fold. The cells were then disrupted by passing them through a Manton-Gaulin homogenizer at 4.1–5.5×10$^4$ kpa (0.6–0.8 psi). After the initial pass sodium dodecyl sulfate (SDS)-sodium phosphate buffer was added to a final concentration of 2% w/v SDS, 0.08M sodium phosphate, and solubilization was continued for one hour. Solid dithiothreitol (DTT) was then added to a final concentration of 50 mM and the homogenate was treated to 90±5° C. for 10 minutes. The resulting cell suspension was extracted with 2-butanol at a 1:1 2-butanol:suspension volume ratio in a static mixer. The mixture was then centrifuged and the 2-butanol-rich phase was collected.

The 2-butanol-rich phase was mixed with 2.5 volumes of 0.1% w/v SDS in phosphate buffered saline (PBS). Solid DTT was added to a final concentration of 1 mM. The pH of the mixture was adjusted to 6.2±0.1 with glacial acetic acid and this mixture was centrifuged. The resulting paste was collected and resuspended in a mixture of PBS and 10% w/v SDS with pH adjustment to 8.5±0.1 using 1N NaOH. Solid DTT was added to a final concentration of 100 mM and the suspension was heated to 90±5° C. for 10 minutes. The suspension was then cooled to about 25° C., the pH was adjusted to 5.5±0.1 with glacial acetic acid, and the solution was filtered.

The solution was then applied to a Sephacryl S-200 precolumn with a buffer consisting of 1% SDS, 50 mM sodium acetate, 1 mM EDTA, pH 5.5. The fractions containing highest interferon activities were pooled and concentrated by ultrafiltration with a 10 kilodalton molecular weight cut-off.

The protein was oxidized to generate sulfhydryl bonds using the method of Shaked, et al., supra. A 1 mM o-iodosobenzoic acid solution was prepared by mixing the acid in water, sonicating the mixture for about 5 minutes and then stirring and adding 2% NaOH slowly to obtain a final pH of 8.2±0.2 (additional sonication may be used as an alternative to adding base).

A reaction buffer medium was prepared by dissolving $Na_4P_2O_7.10H_2O$ in water to a concentration of 2 mM. The pH of this solution was adjusted to 9.0 by adding 10% acetic acid, SDS to 0.1%, ethylenediaminetetraacetic acid (EDTA) to 1 mM and the o-iodosobenzoic acid solution to 15 $\mu$M were added to the solution.

The buffer medium was placed in a reaction vessel equipped with a magnetic stirrer and a pH electrode set at 9.0. The IFN-$_{ser17}$ preparation and the o-iodosobenzoic acid solutions were added to the reaction mixture from holding vessels using peristaltic pumps that were calibrated to introduce equivalent mole ratios of the IFN and oxidizing agent. The pH of the reaction mixture was controlled at 9.0 by adding 0.25M NaOH via a peristaltic pump at 5 ml/hr as needed. The IFN-$\beta$ solution (5 mg/ml in 50 mM acetate buffer, pH 5.5) was added at a flow rate of 2 ml/hr (7.0 micromole/hr) for about 5 hours; the o-iodosobenzoic acid solution was added at 7 ml/hr (7 micromole/hr) over the same time period. The addition of the acid solution was continued thereafter to get a final excess of 10–15 micromolar. The reaction was followed by reverse phase HPLC and by assaying the residual thiol content of IFN-$\beta_{ser17}$ by Ellman's assay. After 6.5 hours the reaction was terminated by adding 10% acetic acid to the reaction mixture to a pH of 5.5.

The product was then loaded on a Sephacryl-200 column using a buffer consisting of 0.1% SDS, 1 mM EDTA, and 50 mM sodium acetate at pH 5.5. The monomer peak from this column was pooled and loaded on a Sephadex G-75 column using a buffer consisting of 0.1% SDS, 1 mM EDTA, and 50 mM sodium acetate at pH 5.5.

Oxidation of Fully Reduced IFN-$\beta_{ser17}$

The Sephadex G-75 pooled material which had been oxidized using the above iodosobenzoic acid oxidation method was employed for the following copper oxidation studies because it was the only interferon product readily available. The purified IFN-$\beta_{ser17}$ was reduced for 15 minutes at 50° C. following addition of dithiothreitol to 10 mM to ensure that none of the molecules contained disulfide linkages. This was confirmed by RP-HPLC in a 30–60% acetonitrile gradient (30–40% in 5 min, 40–60% in 27 min) in 0.1% v/v trifluoroacetic acid (using a Vydac C4 column), which separates the oxidized from the reduced form of interferon (retention times 26 and 28 min, respectively). The reduced $\beta$-interferon was concentrated from the RP-HPLC peak fraction by lyophilization and resuspension in 0.1% w/v SDS and 50 mM phosphate buffer at pH 7.0 containing 5 micromolar EDTA. The reaction mixture contained 0.13 mg/ml of the interferon. Oxidation was initiated by adding $CuCl_2$ to a final concentration of 8 micromolar using air-saturated solutions at 25° C.

It has been shown by others that the kinetics of disulfide formation can be measured by monitoring changes in elution position from various HPLC columns (Wu, et al., *Anal. Biochem.*, 129, 345–348 (1983) and Reference 8 therein). One assay for oxidation used in the present examples relies on a shift in elution position on RP-HPLC following oxidation.

FIG. 1A illustrates RP-HPLC of a control reaction containing the reduced $\beta$-interferon after 7 minutes in the resuspension media without $CuCl_2$. FIG. 1B illustrates RP-HPLC of the reaction mixture containing $CuCl_2$ after 7 minutes of oxidation, FIG. 1C, after 14 minutes of oxidation, FIG. 1D, after 28 minutes of oxidation, and FIG. 1E, after 75 minutes. FIG. 1F illustrates a plot of percent oxidation versus minutes of oxidation based on the RP-HPLC analysis. The results show that the interferon is more than 95% oxidized by 75 minutes. This oxidized product was assayed for antiviral activity using the cytopathic effect assay described by Steward, W. E. II, *The Interferon System*, (New York:Springer-Verlag, 1981), p. 17, and was found to have the same specific bioactivity as native $\beta$-IFN, $1\times 10^8$ units/mg.

The sample which was oxidized for 75 minutes was then reduced in 10 mM DTT at 50° C. for 15 minutes. FIG. 2A shows the RP-HPLC of the oxidized material and FIG. 2B shows the RP-HPLC of the reduced material. Comparison of the chromatograms indicates that the shift in RP-HPLC retention time was due to an oxidation which was reversible by DTT reduction.

EXAMPLE 2

Controlled Oxidation of Des-Ala IL-2$_{ser125}$

Preparation of Fully Reduced Des-Ala IL-2$_{ser125}$

Des-ala IL-2$_{ser125}$ is an IL-2 whose amino acid sequence differs from native human IL-2 by: (1) the absence of the initial N-terminal alanine residue and (2) a serine substituted for cysteine at position 125. The strain of des-ala IL-2$_{ser125}$-producing *E. coli* used for this example was deposited in the ATCC on Mar. 6, 1984 under accession No. 39,626.

The genetically engineered *E. coli* mentioned above was grown in a fermenter using the following growth medium:

| | Approximate Initial Concentration |
|---|---|
| Initial Ingredients Added: | |
| $(NH_4)_2SO_4$ | 72 mM |
| $KH_2PO_4$ | 21.6 mM |
| $Na_3$ Citrate | 1.5 mM |
| $ZnSO_4.7H_2O$ | 60 $\mu$M |
| $MnSO_4.H_2O$ | 60 $\mu$M |
| $CuSO_4.5H_2O$ | 2 $\mu$M |
| pH adjusted to 6.50 with 2.5 N NaOH | |
| Autoclaving | |
| Sterile Additions (post autoclave): | |
| $MgSO_4.7H_2O$ | 3 mM |
| $FeSO_4$ | 100 $\mu$M |
| L-tryptophan | 70 mg/l |
| Thiamine-HCl | 20 mg/l |
| Glucose | 5 g/l |
| Tetracycline | 5 mg/l |
| Ethanol (optional) | 2% (w/v) |
| Casamino acid | 2% (w/v) |

A 20% solution of Dow Corning Antifoam B, a 50% solution of glucose and 5N KOH were added on demand.

The pH of the fermenter was maintained at 6.8 with 5N KOH. Residual glucose was maintained between 5–10 g/l, dissolved oxygen at 40% w/w, and temperature at 37±1° C. The casamino acids (20% w/v stock solution) were added when the $OD_{680}$ was about 10–15. Three hours after adding the casamino concentrated solution, ethanol (95% w/w) was added to achieve a final 2% w/w concentration. Harvest was made two hours after ethanol addition.

About 20–40 g (wet weight) of the E. coli MM294-1 cells containing the induced, cloned IL-2 were resuspended in 200 ml of 50 mM Tris, 1 mM EDTA (pH 8.1 to 8.5). The high pH aided in selective extraction of E. coli proteins in subsequent steps. The cells were centrifuged at 3000–4000×g for 10 minutes and resuspended in 200 ml of Tris/EDTA buffer at 4° C.

The cells were then sonicated at 4° C. for 45 minutes (or until the optical density at 600 had dropped about 85%) using large probe pulsing with 50% duty on power setting "9" of Heat Systems Model W-375 sonicator. Alternatively the cells were broken by three passes through a Manton-Goulin homogenizer. The homogenate was centrifuged at 4500×g for 10 minutes (6000 rpm) using a Beckman JA20 rotor at 4° C. The debris was resuspended in 60 ml of a Tris/EDTA mixture at room temperature. Over a period of 5 minutes an equal volume of 8M urea (Schwartz/Mann ultra pure) in Tris/EDTA buffer was added to the suspension with rapid stirring to yield a final urea concentration of 4M. The resulting mixture was stirred slowly for 15–30 minutes at room temperature.

After stirring the mixture was centrifuged at 12,000×g for 15 minutes (12,000 rpm in Beckman JA20 rotor at room temperature) and the pellet was saved. The pellet was then resuspended in 9 ml of 50 mM sodium phosphate (at pH 6.8), 1 mM EDTA, 10 mM DTT at 20° C. The pellet was then solubilized by addition of 1 ml of 20% w/v SDS and vortexed vigorously. The resuspension was centrifuged at 12,000×g for 10 minutes at room temperature and the insoluble material was discarded.

The remaining solution was heated to 40° C. for 15 minutes to ensure that all of the IL-2 was fully reduced. The supernatant fluid (containing 40% pure IL-2) was loaded onto a 2.6 cm×100 cm Sephacryl-200 (S-200) column run in 50 mM sodium phosphate (pH 6.8), 1 mM EDTA, 1 mM DTT, 1% w/v SDS. Then 3 µl aliquots of each fraction were run on a 15% w/v SDS/PAGE minigel and the gel was stained with Coomassie blue. The fractions with the fewest contaminants (minimizing the inclusion of contaminants at about 35K, 18K and 12K daltons) were pooled and concentrated to 5–10 ml using an Amicon YM5 ultrafilter. The preparation was about 80–90% pure IL-2.

The S-200 pool was loaded onto a 2.6 cm×100 cm Sephadex G-100 column, which was eluted as described above using 0.1% w/v SDS. The fractions were analyzed by SDS/PAGE and the purest fractions pooled. These purest fractions contained 95–98% pure IL-2 with 0.2–0.5 ng of endotoxin per 100,000 units. Over 30% of the IL-2 present in the crude lysate was recovered as pure IL-2.

When stored at 4° C. under nitrogen these pooled G-100 fractions were found to be stable for at least six weeks without additions. An SDS-containing precipitate formed at 4° C. which could be redissolved at 25° C. prior to use or could be removed without significant loss of IL-2 units.

Controlled Oxidation of Des-Ala IL-2$_{ser125}$ Using CuCl$_2$

The purified, fully reduced product obtained as described above was adjusted to 0.5 mg/ml IL-2 by diafiltration/ultrafiltration against 50 mM Tris-HCl buffer at pH 8.0. Diafiltration against Tris buffer acted not only to adjust pH but also removed any remaining EDTA or DTT which might interfere with the oxidation reaction. The SDS concentration after the diafiltration/ultrafiltration step was 1.6% w/v (as measured by the acridine orange assay for SDS described in Anal. Biochem., Vol. 118, p. 138–141 (1981)), and the pH was about 8.0. The concentrate was oxygenated by bubbling air through the solution, and the oxidation was initiated by adding CuCl$_2$ to 0.5 µM, 5 µM, or 50 µM using freshly prepared solutions. Reactions were carried out at 25° C. For determining the kinetics of oxidation, aliquots of the reaction mixtures were taken at various time intervals and quenched by adding EDTA up to 10 mM concentration and quick freezing at −70° C. Each aliquot was analyzed by RP-HPLC using acetonitrile gradient elution (30–60% in 45 min) in 0.1% trifluoroacetic acid to determine the extent of reaction, because RP-HPLC separates the oxidized from the reduced form of the IL-2 (retention times 41 and 45 min, respectively).

FIG. 3 shows the RP-HPLC analysis of the oxidation reactions using 50 µM CuCl$_2$ (before and after re-reduction). FIG. 3A shows that after only 2 minutes of oxidation the sample was approximately two-thirds oxidized. FIG. 3B shows that after 10 minutes of oxidation the sample was essentially entirely oxidized, and only traces of other peaks (indicative of side reactions) were observed. FIG. 3C shows that 50 minutes of oxidation did not increase the amounts of the minor product components produced, and therefore that side reactions do not occur during prolonged oxidation. FIG. 3D shows that the oxidation product after 50 minutes of oxidation can be re-reduced to the fully reduced IL-2 using 10 mM dithiothreitol for 15 minutes at 60° C. This indicates that the peaks in FIGS. 3A, 3B and 3C represented oxidized material which was reducible.

FIG. 4 shows a silver-stained non-reducing SDS-PAGE analysis of the product of 40 minutes of oxidation using 50 µM CuCl$_2$. Despite the sensitive staining technique employed, only a trace of the oxidized product was found to have formed intramolecular sulfhydryl groups, generating dimers.

The studies of oxidations performed at various CuCl$_2$ concentrations are summarized graphically in FIG. 5. This figure shows that the observed oxidation rate as measured by HPLC peak height, less background, is dependent on CuCl$_2$ concentration, and therefore the reaction can be controlled by adjusting this parameter. The reaction using 5 µM CuCl$_2$ contained a 6-fold molar excess of IL-2, yet was completely oxidized in 60 minutes, indicating that the CuCl$_2$ may act catalytically. A control reaction, containing 10 mM EDTA, showed essentially no oxidation.

A similar series of oxidations was conducted on a 0.2 mg/ml IL-2 solution using 8 µM CuCl$_2$ in a mixture of 30 mM Tris and 30 mM sodium phosphate buffer adjusted to pH 6, 6.5, 7.5, 8.0, 8.5 or 9.5 and containing 0.1% w/v SDS. In all reactions the pH was confirmed at the end of the reaction. The studies of oxidations performed at these pH values for 7 minutes are summarized graphically in FIG. 6. This figure shows that there is an optimum pH range for oxidation of IL-2: about 6 to 8, above which the oxidation rate falls off dramatically.

Controlled Oxidation of Des-Ala IL-2$_{ser125}$ Using (o-Phenanthroline$_2$Cu$^{+2}$ Complex The above oxidation procedure was repeated using a freshly prepared 8 μM (o-phenanthroline)$_2$Cu$^{+2}$ complex instead of CuCl$_2$. The Tris/phosphate buffer described above was employed at pH 7.0, containing 0.1% SDS (w/v). FIG. 7 gives a comparison of the RP-HPLC for the IL-2 after 7 minutes of oxidation with 8 μM CuCl$_2$ (FIG. 7A) with the RP-HPLC for the IL-2 after 7 minutes of oxidation with 8 μM (o-phenanthroline)$_2$Cu$^{+2}$ (FIG. 7B). The results show that IL-2 can be more rapidly oxidized by (o-phenanthroline)$_2$Cu$^{+2}$ complex at pH 7 than by CuCl$_2$ alone.

Purification of Oxidized Des-Ala IL-2$_{ser125}$

The insoluble material recovered from the urea extraction of Example 2 was resuspended in 50 mM sodium phosphate buffer, 1 mM EDTA pH 7.0. The suspension was then solubilized by addition of solid SDS to a final concentration of 5% w/v.

The 5% SDS solution was diluted to 2% SDS with 0.1M Na$_2$PO$_4$, pH 8.0. The protein concentration was determined, the pH was adjusted to 8.5, and DTT to 50 mM and EDTA to 2 mM were added. The mixture was heated to 40° C. under N$_2$ to reduce the IL-2. The mixture was then cooled and the pH was adjusted to 5.0.

The solution was then extracted at a 1:1 ratio (v/v) with 2-butanol containing 1 mM DTT at room temperature. Residence time was 2-2.5 minutes. The extraction was carried out in a liquid-liquid phase separator using a flow rate of 200 ml/min. The organic extract was separated and its pH was adjusted to 8.0 with NaOH. The extract was then added slowly to 0.1% SDS in 10 mM Na$_2$PO$_4$, 2 mM DTT, pH 6 and stirred for 15-20 minutes. The resulting precipitate was separated and the resulting paste was resuspended in 5% SDS in PBS. The solution was clarified by centrifugation and reduced as above. Following reduction the solution was adjusted to pH 5.5 with acetic acid. The solution was purified by gel filtration using a 2.6 cm×100 cm S-200 column run in 50 mM sodium phosphate (pH 6.8), 1 mM EDTA, 1 mM DTT, 1% w/v SDS.

The peak fractions from this column were pooled, and a portion of this material (in 50 mM sodium acetate (pH 5.5), 1% SDS, 2 mM DTT and 1 mM EDTA) was concentrated to 760 microliters using an Amicon YM-5 ultrafiltration membrane, yielding 6.6 mg of total protein. Dithiothreitol was added to a concentration of 2.5 mM, and the sample was heated to 60° C. for 10 minutes to ensure full reduction. Reducing agent was removed using a G-25 desalting column (19×0.9 cm) equilibrated in 50 mM sodium phosphate buffer (pH 7.0) containing 0.1% SDS. The protein peak was pooled, yielding 5.5 mg, which was diluted to 0.25 mg/ml in column buffer. The amount of free sulfhydryl groups was immediately assayed using the Ellman's reagent (5,5'-dithio-bis(2-nitrobenzoic acid), (DTNB)) sulfhydryl assay (as described by Habeeb, A.F.S.A., *Methods of Enzymology*, vol. 25, Part B, pp 457-64 (1972) using cysteine as a standard).

Air was bubbled through the sample for 15 seconds to aerate the solution, and oxidation at 25° C. was initiated by addition of CuCl$_2$ to a concentration of 50 micromolar. The extent of oxidation was measured by assaying residual free sulfhydryl groups essentially using the DTNB assay after 5, 10, and 30 minutes of room temperature incubation.

Figure 8:
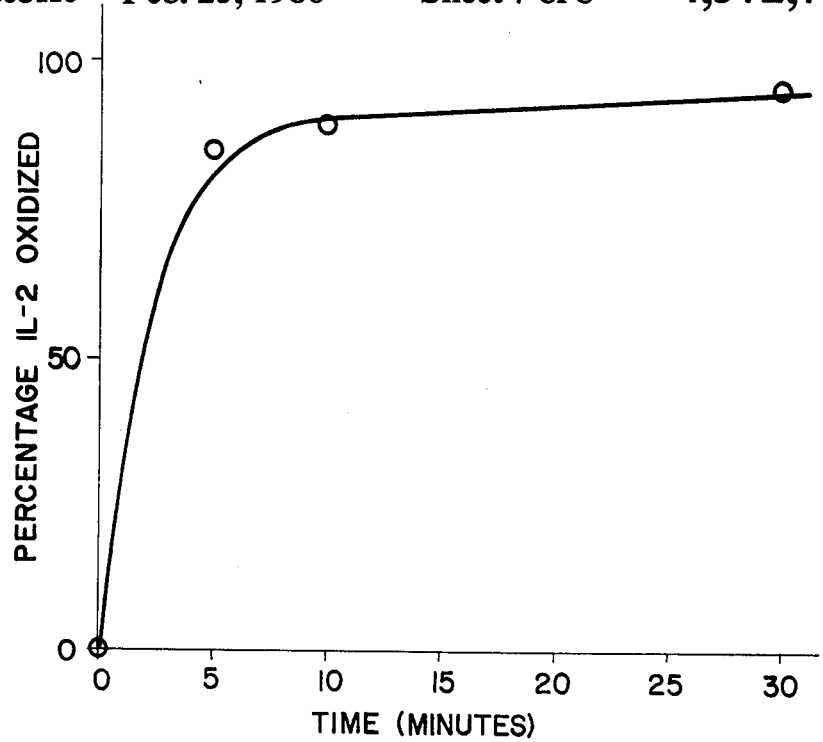
FIG. 8 represents a graph of the percentage of des-ala IL-2$_{ser125}$ oxidized (the disappearance of free sulfhydryl groups as measured by reaction with DTNB) as a function of time in minutes at 25° C. using 50 µM CuCl$_2$, 0.25 mg/ml partially purified IL-2, 50 mM sodium phosphate, 0.1% SDS, at pH 7.0.

FIG. 8, which depicts the kinetics of oxidation of the peak IL-2 fractions from the S-200 column, shows that oxidation was essentially complete by 30 minutes. EDTA was added to a concentration of 10 mM at 35 minutes, followed by addition of one-tenth volume of 100% acetonitrile/5% trifluoroacetic acid. The oxidized IL-2 was then separated from remaining *E. coli* protein and endotoxin by preparative RP-HPLC on a 10 mm×25 cm, 10 micron Vydac C4 column equilibrated in 10% acetonitrile/0.1% TFA. IL-2 was recovered at 60% acetonitrile following gradient elution at 2 ml/min. (10-30% acetonitrile in 5 minutes, 30-60% acetonitrile in 45 minutes). The peak of IL-2 was pooled, and the total protein recovered was determined to be 3 mg by absorption at 280 nm.

At this point the protein was formulated as follows: to a volume of 7.7 ml pooled HPLC fractions mannitol was added to 1.7%, and SDS was added to 0.037%. The sample was lyophilized overnight and resuspended in 2.9 ml of 50 mM sodium phosphate (pH 6.8) in WFI (water for injection). The final concentrations of SDS and mannitol were 0.1% and 5%, respectively.

Figure 9:
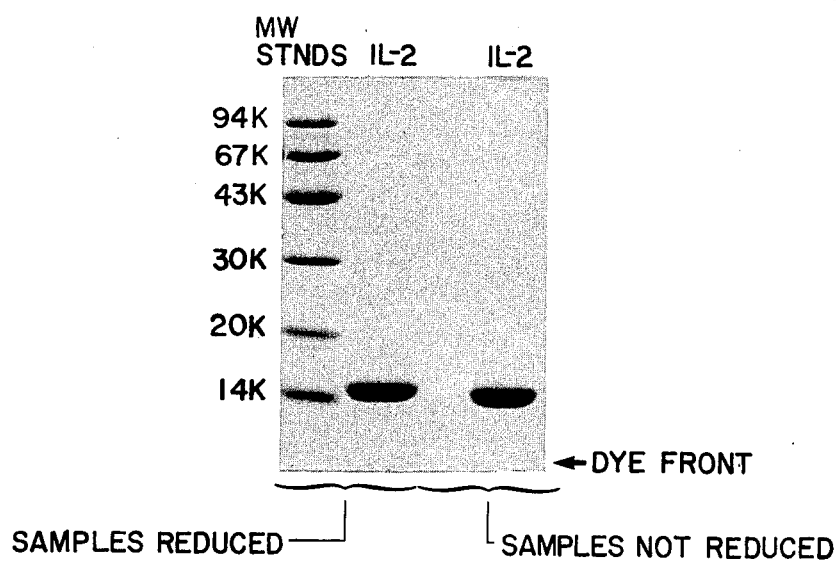
FIG. 9 represents a SDS-PAGE analysis of both a reducing and non-reducing gel of the HPLC-purified IL-2 oxidized using 50 µM CuCl$_2$.

Four micrograms of the lyophilized, resuspended IL-2 was subjected to SDS-PAGE minigel analysis under reducing and non-reducing conditions (boiling 5 minutes in 2% SDS, 50 mM tris-HCl, pH 6.8, with or without 1% β-mercaptoethanol). The analysis, given in FIG. 9, shows that the non-reduced IL-2 migrated slightly faster than the reduced IL-2, as expected from the literature for a molecule containing disulfide bonds. Densitometric scans using the Shimadzu CS-930 scanner of the TCA-fixed, Coomassie-stained gel showed that the final product is over 95% pure and contains less than 2% protein migrating in the positions expected for oligomeric IL-2. Where necessary, residual IL-2 oligomers can be effectively eliminated by molecular sieve chromatography (S-200 columns, run as described above) following the IL-2 oxidation step. The RP-HPLC appeared to remove both residual *E. coli* contaminants and pyrogens. At least 50% of the pooled S-200 starting material was recovered in the final oxidized product.

The final specific bioactivity of the purified IL-2 was measured to be 4-6×10$^6$ units/mg (units based on units measured with the HT-2 cell proliferation assay (Watson, J. (1979) *JEM*, 150:1510-1519 and Gillis, S., et al. (1979) *J.I.*, 120:2027-2032) and on protein content measured by the method of Lowry, O. H., et al. (1951) *J. Biol. Chem.*, 193:265-275), and the endotoxin content was less than 0.3 nanograms/mg IL-2, as measured by limulus amoebocyte lysate (LAL) assay. The specific biological activity of the purified oxidized product is essentially indistinguishable from that of native IL-2 from induced periferal blood lymphocytes or the native IL-2 isolated from the induced Jurkat cell line. Thus, the oxidized, recombinant IL-2 bioactivity resembles that of two native counterparts which are known to be oxidized. Reduced native and reduced recombinant IL-2 proteins both have significantly lower specific bioactivities. Because the oxidized product herein was shown to have biological activities identical to those measured for native Jurkat or peripheral blood lymphocyte IL-2 (unpublished observations), IL-2 produced by the present process may be useful in enhancing the ability of the human immune system to combat viral pathogens and cancers.

The final product may be lyophilized for storage, and/or may be stored in solution at 4° C. for up to 60 days or more without significant change in biological or physical properties.

When the oxidation reaction of des-ala IL-2$_{ser125}$ was conducted as described above but without using SDS or another solubilizing agent to keep the fully reduced IL-2 in solution, no measurable oxidation took place. When the oxidation was carried out on des-ala IL-2$_{ser125}$ using the preferred conditions described above except using FeSO$_4$ as the oxidation promoter, less than 10% of the product had been oxidized, indicating that Fe$^{+2}$ is much less effective a cation for promoting oxidation.

When the oxidation was carried out on a reduced molecule containing three cysteines (i.e., des alanyl, recombinant IL-2 produced from an *E. coli* strain deposited in the American Type Culture Collection on Aug. 4, 1983 under accession no. 39,405) using the conditions described above, at least 85% of the product had the correct disulfide linkage (between cys 58 and cys 105) and showed identical bioactivity to the native protein. Approximately 15% of the material was inactive, presumably representing isomers of IL-2 which contain incorrect disulfide linkages. FIG. 10 shows a RP-HPLC analysis of the final product eluted with a 30-60% acetonitrile gradient. The retention times are 29 min for inactive isomers and 44 min for active IL-2.

EXAMPLE 3

Controlled Oxidation of Des-Ala IL-2$_{ser125}$ at 37° C.

This example illustrates the effect of increased temperature on the oxidation reaction of this invention.

The peak fractions from the S-200 column described in Example 2 under Purification of Oxidized Des-Ala IL-2$_{ser125}$ were pooled and the peak material was concentrated to 720 microliters using an Amicon YM-5 ultrafiltration membrane. Dithiothreitol was added to a concentration of 3.5 mM, and the IL-2 was then heated to 60° C. for 10 minutes. The dithiothreitol was then removed using a G-25 desalting column equilibrated in 50 mM sodium phosphate buffer (pH 7.0) containing 0.1% SDS. The protein concentration was adjusted to 0.25 mg/ml using the same buffer. The IL-2 was then divided into two 10-ml portions and equilibrated at either 25° C. or 37° C. in a circulating water bath. The oxidation was initiated by adding CuCl$_2$ to 50 μM. The kinetics of oxidation were then determined by (1) measuring the amount of free sulfhydryl groups using the Ellman's reagent assay, and (2) monitoring the amount of IL-2 present at the retention times expected for reduced and oxidized IL-2 following RP-HPLC.

Raising the temperature of oxidation from 25° C. to 37° C. increased the rate of oxidation approximately two-fold as measured by both assays. Thus, temperature, as well as copper concentration, has an effect on oxidation rate. Both the oxidations at 25° C. and 37° C. proceeded to essentially 100% completion, thereby minimizing free sulfhydryl groups and greatly diminishing the possibility of subsequent oligomer formation by thio-disulfide exchange. Reverse phase HPLC analysis revealed that the oxidized IL-2 products appeared identical, and bioassay showed that they had the same specific activity. Non-reducing SDS-PAGE analysis demonstrated that less than 1% oligomers had been formed at either temperature.

In summary, the present invention is seen to provide a controlled method of oxidizing fully reduced cysteine-containing recombinant IL-2 and IFN-β using an oxidation promoter containing Cu$^{+2}$ which catalyzes the in vitro formation of disulfide bridges which correspond to those found in the native proteins. The process herein eliminates or minimizes side reactions during the oxidation and maximizes the ability of the oxidized product to regain full bioactivity.

Modification of the above-described modes for carrying out the invention that are obvious to those of skill in biochemical engineering are intended to be within the scope of the following claims.

What is claimed is:

1. A method of oxidizing a fully reduced recombinant protein selected from the group consisting of interferon-beta, interleukin-2 and muteins thereof, whereby cysteines are oxidized preferentially to form the disulfide bridges which correspond to those present in the naturally occurring protein, which method comprises reacting an aqueous solution containing a solubilized form of the recombinant protein at a pH between about 5.5 and 9 in the presence of air with at least an effective amount of an oxidation promoter containing a Cu$^{+2}$ cation.

2. The method of claim 1 wherein the recombinant protein is a mutein of said protein having at least one of its cysteine residues which is free to form a disulfide bond and is nonessential to the biological activity of the protein deleted or replaced by another amino acid.

3. The method of claim 2 wherein the mutein is des-ala IL-2$_{ser125}$.

4. The method of claim 2 wherein the mutein is IFN-β$_{ser17}$.

5. The method of claim 1 wherein the pH is between about 6 and about 8.

6. The method of claim 1 wherein the pH is about 7.

7. The method of claim 1 wherein the oxidation promoter is CuCl$_2$ or (o-phenanthroline)$_2$Cu$^{+2}$.

8. The method of claim 1 wherein the oxidation promoter is CuCl$_2$.

9. The method of claim 1 wherein the oxidation promoter is (o-phenanthroline)$_2$Cu$^{+2}$.

10. The method of claim 1 wherein the concentration of said protein is in the range of about 0.05 to about 2 mg/ml.

11. The method of claim 1 wherein the concentration of said oxidation promoter is approximately equivalent to the concentration of free sulfhydryl groups on the protein which are intended to be oxidized to form cystines.

12. The method of claim 10 wherein the oxidation promoter is CuCl$_2$ and its concentration ranges from about 1 to 400 micromolar.

13. The method of claim 1 wherein the reaction is carried out at a temperature of from 20° to 40° C.

14. The method of claim 1 wherein the protein is solubilized with sodium dodecyl sulfate.

15. The method of claim 14 wherein the concentration of sodium dodecyl sulfate prior to reaction ranges from about 0.05% to 2% by weight per volume.

16. The method of claim 1 wherein the protein is an IL-2 or IFN-β mutein, the oxidation promoter is CuCl$_2$ in an amount of from about 5 to 50 micromolar, the pH of the reaction is about 7, the concentration of IL-2 in the reaction mixture ranges from about 0.1 to about 1 mg/ml, and sodium dodecyl sulfate is present as a solubilizing agent at a concentration ranging from about 0.1 to 1% by weight per volume.

17. The method of claim 16 wherein the mutein is des-ala IL-2$_{ser125}$.

18. The method of claim 16 wherein the mutein contains the three cysteines present in native IL-2.

19. The method of claim 16 wherein the mutein is IFN-β$_{ser17}$.

* * * * *